United States Patent [19]
Xie et al.

[11] Patent Number: 5,728,290
[45] Date of Patent: Mar. 17, 1998

[54] POLAROGRAPHIC SENSOR AND METHOD OF USING SAME

[75] Inventors: Yougin E. Xie, Diamond Bar; Dean Y. Lin, Chino Hills; Khan V. Nguyen, Westminster; Frank R. Shu, La Habra Heights, all of Calif.

[73] Assignee: Beckman Instruments, Inc., Fullerton, Calif.

[21] Appl. No.: 665,578

[22] Filed: Jun. 3, 1996

[51] Int. Cl.$^6$ .................................................. G01N 27/404
[52] U.S. Cl. ........................ 205/783; 204/415; 205/782.5
[58] Field of Search ................................ 204/415, 431, 204/432; 205/782.5, 783

[56] References Cited

U.S. PATENT DOCUMENTS

| | | |
|---|---|---|
| 2,913,381 | 11/1959 | McFadyen et al. . |
| 3,278,408 | 10/1966 | Leonard et al. ............... 204/415 |
| 3,429,796 | 2/1969 | Lauer ........................... 204/415 |
| 3,449,231 | 6/1969 | Adams et al. ................. 204/415 |
| 3,493,484 | 2/1970 | Berg et al. .................... 204/431 |
| 3,575,836 | 4/1971 | Sternberg ..................... 204/415 |
| 4,062,750 | 12/1977 | Butler ........................... 204/279 |
| 4,198,280 | 4/1980 | Swartz ........................... 204/415 |
| 4,248,712 | 2/1981 | Bauermeister ............... 204/415 |
| 4,466,878 | 8/1984 | DiNitto et al. . |
| 4,563,249 | 1/1986 | Hale .............................. 204/415 |
| 5,202,011 | 4/1993 | Kiesele et al. . |
| 5,344,546 | 9/1994 | Kiesele et al. ............... 204/415 |

OTHER PUBLICATIONS

"Polarographic Oxygen Sensor", Irving Fatt, 1975 month unavailable, CRC Press, Cleveland.

"Transactions of the American Society for Artificial Internal Organs", L.C.Clark, Jr., vol. 2, 1956/1957 month unavailable.

"Membranes: Separation Principles and Sensing", M.B. McDonnell and P.M. Vadgama, *Selective Electrode* Rev. 1989 month unavailable, vol. 11, pp. 17–67.

Advances in Biochemical Engineering, Y.H. Lee and G.T. Tsao, 1978 month unavailable, 13:35.

*Primary Examiner*—T. Tung
*Attorney, Agent, or Firm*—William H. May; Margaret A. Kivinski; Sheldon & Mak

[57] ABSTRACT

A polarographic sensor device to determine the partial pressure of a gas in a sample medium is disclosed. The device comprises a) a substantially hydroscopic electrolyte composition joining a pair of spaced apart electrodes, one of the pair of electrodes being a sensing electrode; b) a membrane permeable to gas but impermeable to the electrolyte, the membrane having a front section for separating the electrodes and the electrolyte from the sample medium; and c) a fastener comprising a sleeve having a body portion and a lip, the body portion retaining the fastener and a side section of the membrane, and the lip retaining a portion of the front section of the membrane and holding substantially the entire front section in a spaced apart relationship from the sensing electrode.

34 Claims, 3 Drawing Sheets

POLAROGRAPHIC SENSOR AND METHOD OF USING SAME

BACKGROUND

Polarographic oxygen sensors have widespread applications in the fields of biology, chemistry and medicine. These sensors provide a useful analytical technique for detecting and measuring the partial pressure of a gas in a test sample. The applications of sensors are numerous including biomedical research, clinical testing, industrial pollution testing and chemical-process control.

Particularly, in biochemical and chemical applications, polarographic sensors can provide a convenient analysis for measuring a variety of substances including gases such as oxygen and carbon dioxide.

Polarographic sensors can be important in the diagnosis and treatment of diseases due to their ability to measure partial pressures of gases that are changing during various enzymatic assays of bodily fluids. Such bodily fluids include blood, serum, plasma, cerebral spinal fluid and urine samples. For example, the measurement of glucose concentration levels is important in clinical settings since glucose levels can be characteristic of certain metabolic disorders including diabetes. Spectrophotometric and electrochemical methods can be used to analyze glucose concentrations. However, disadvantages associated with these methods are that they can often require an additional purification step to eliminate tissues which could interfere with the assay. In order to overcome these problems, polarographic sensors are used to measure the oxidation of glucose in blood and urine with glucose-oxidase enzyme.

Similarly, measurements of catalase activity in cerebral spinal fluid are used in the diagnosis of diseases in the central nervous system such as brain hemorrhaging.

For medical purposes, polarographic sensors typically measure rate measurements as opposed to industrial purposes which measure steady state reactions. In particular with medical applications, it is imperative to have a sensor that has a fast response in order to measure rate changes.

Recent designs of polarographic sensors comprise a pair of electrodes, one of the electrodes being a sensing electrode, joined by an electrolyte with a single or multilayer gas permeable membrane separating the electrodes and electrolyte from the sample medium. In this type of sensor, when a suitable voltage is applied across the electrodes, the current passed between the electrodes is in proportion to the partial pressure of the gas in the sample. In the absence of a gaseous component in the sample that is to be analyzed, the electrode system becomes polarized so that the current which normally flows through the electrolyte is reduced to nearly zero after a short period of time. In the presence of the component to be analyzed, the electrode system becomes depolarized and current flows again.

The magnitude of the current in these sensors is a function of the rate or speed with which the component to be analyzed can pass through the membrane and of the diffusion processes that take place in the membrane. The permeability characteristics of the membrane and the spatial relationship between the membrane and the electrode can be extremely important since the component to be analyzed has to pass through the membrane and the electrolyte disposed between the membrane and the sensing electrode.

However, a disadvantage associated with these sensors is the difficulty in maintaining a good spatial relationship between the electrode and the membrane which can result in a shift in the calibration reading of the sensors. Further disadvantages associated with these sensors are instability in the electrical output of the sensors. In order to overcome these problems, the membrane can be "tightly squeezed" towards the sensing electrode surface. However, a disadvantage associated with sensors of this type is the drying out of the electrolyte between the membrane and the sensor which can lead to an inoperable polarographic sensor. In addition, a further disadvantage with these sensors is that due to the high tension placed upon the membrane, a cold flow can take place which can change the tension of the membrane from the tension which was originally applied. As a consequence, the spatial relationship between the membrane and the sensing electrode changes and thus, the response of these sensors does not remain constant which can attribute to inconsistencies and variability in these polarographic sensors performance. In most cases, the electrode membrane and the electrolyte solution require changing on a weekly basis to ensure a properly maintained and functioning electrode. This process can be tedious and can result in unsatisfactory performance.

For the foregoing reasons, there is a need for a polarographic sensor which exhibits fast and stable response time, and excellent reliability of accurately detecting and measuring a gas being analyzed in a sample medium. Further, it would be advantageous to have this polarographic sensor to be able to maintain its performance for prolonged periods of time.

SUMMARY

A polarographic sensor device to determine the partial pressure of a gas in a sample medium is disclosed. The device comprises a) a substantially hydroscopic electrolyte composition having a relatively low concentration of electrolyte joining a pair of spaced apart electrodes, one of the pair of electrodes being a sensing electrode; b) a membrane permeable to gas but impermeable to the electrolyte, the membrane having a front section for separating the electrodes and the electrolyte from the sample medium; and c) a fastener comprising a sleeve having a body portion and a lip, the body portion retaining the fastener and a side section of the membrane, and the lip retaining a portion of the front section of the membrane and holding substantially the entire front section in a spaced apart relationship from the sensing electrode.

The membrane of the device, separates the electrodes and the electrolyte from the sample medium and the membrane is in a spaced apart relationship from the sensing electrode.

The sleeve maintains the spaced apart relationship between the membrane and the sensing electrode.

The membrane can be at least one of the following: polyethylene, polypropylene, a polymer of a fluorinated alkane, silicone rubber, polytetrafluoroethylene (Teflon), perfluoroalkoxy polymer and perfluoroalkoxy-Teflon (PFA-Teflon). Preferably, the membrane is perfluoroalkoxy-polytetrafluoroethylene (PFA-Teflon). The thickness of the membrane typically is from about 1 mil to about 3 mils. Preferably, the thickness of the membrane is about 1 mil.

The gas can be oxygen or carbon dioxide.

Typically, the sensing electrode is a cathode made of a wire. The wire can be made of platinum, gold, silver and rhodium. Preferably the wire is rhodium.

The second electrode can be an anode made of a wire. Typically, the wire can be made of zinc, cadmium, lead and silver. Preferably, the wire is silver.

The electrolyte composition can be made of potassium chloride or lithium chloride. Preferably, the electrolyte composition is lithium chloride. The concentration of the lithium chloride solution typically is from about 0.02M to about 0.20M. Preferably, the concentration is from about 0.02M to about 0.10M. More preferably, the concentration of lithium chloride is 0.025M.

The sleeve can be elastomeric. The fastener can further include a gasket for retaining the membrane in a spaced apart relationship.

The electrolyte composition can further include glycerol or ethylene glycol. Typically, when the electrolyte composition includes glycerol, the concentration of glycerol can be from about 5% to about 20%. Preferably, the concentration of glycerol is 10%.

DESCRIPTION OF THE DRAWINGS

These and other features, aspects and advantages of the present invention will become better understood with reference to the following description, appended claims, and accompanying drawings where:

DESCRIPTION

Figure 1:
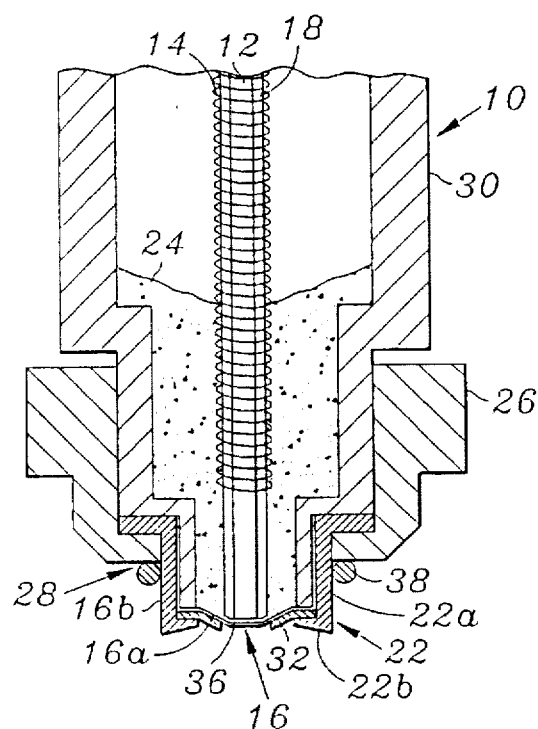
FIG. 1 shows a cross section of an elevational view of a polarographic sensor device according to the present invention.
Figure 2:
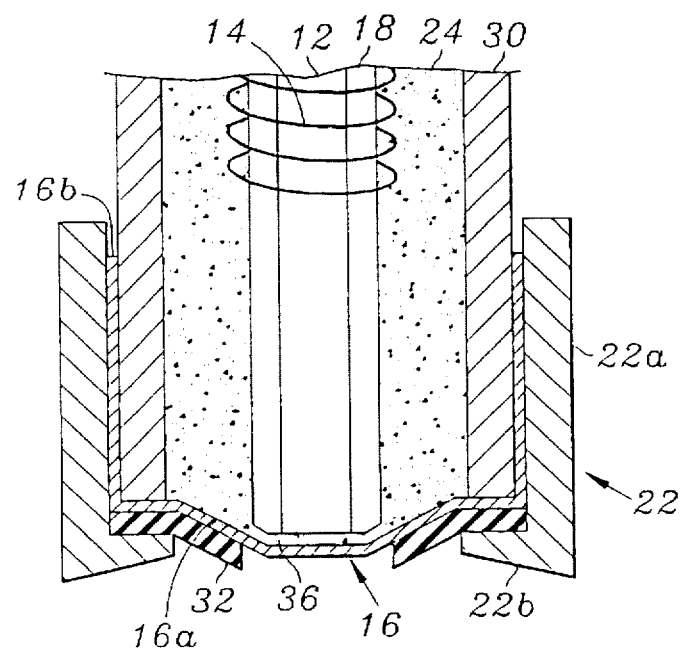
FIG. 2 is a diagram showing an enlarged view of the distal end of the device shown in FIG. 1.

According to one aspect of the present invention, there is provided a solid state polarographic sensor device for measuring a gaseous component in a sample medium which is sensitive, selective and suitable for analytical use. FIG. 1 illustrates a sensor constructed in accordance with the present invention. FIG. 2 illustrates in detail the distal end of the device shown in FIG. 1 showing the relationship between the sleeve and membrane portion of the sensor device. The general operation of polarographic sensors is well known in the art. A detailed description of the general structure of these sensors is provided in U.S. Pat. No. 2,913,381 to Clark Jr., the contents of which are herein incorporated by reference.

As shown in FIGS. 1 and 2, the polarographic sensor device 10 comprises a substantially hydroscopic electrolyte composition 24 joining a pair of spaced apart electrodes, one of the pair of electrodes being a sensing electrode 12. The sensing electrode 12 can be in the form of a wire which is embedded in a plastic or glass body 18. The second electrode 14 surrounds the sensing electrode 12 and has a major portion of the electrode 14 disposed in the electrolyte composition 24. The second electrode can be an anode. The device can further include a housing 30, having an internal cavity, a first end and an outer surface. The membrane 16 has a front section 16a which encloses the first end of the housing. The housing can be tubular shaped.

The device further comprises a fastener having a sleeve 22 with a body portion 22a and a lip 22b. The body portion 22a, retains a side section of the membrane 16b against the side of the housing 30. The lip 22b, retains a portion of the front section of the membrane 16a and holds substantially the entire front section 16a in a spaced apart relationship from the sensing electrode.

During assembly of the polarographic sensor device 10, the membrane 16 is first mounted on to the housing 30. The membrane 16 is tightly drawn over the first end and the outer surface of the housing. An outer elastomeric sleeve 22, such as silicone rubber, is pushed gently over the first end of the housing 30. Next, the internal cavity of the housing is about ⅓ filled with the substantially hydroscopic electrolyte composition 24. The sensing electrode 12 is inserted into the internal cavity of the housing, pressing against the membrane 16 and distending the membrane 16 from a flat cross section to a bulging distended cross section from the first end of the housing. The electrolyte in the internal cavity of the housing is disposed annularly around the sensing electrode 12 and extends throughout the internal cavity of the housing into a region forming an electrolyte film 36 between the membrane 16 and the tip of the sensing electrode 12 to provide an electrically conducting path between the two spaced apart electrodes. A spaced apart relationship is maintained between a back section of the membrane 16 and the sensing electrode 12. The sensing electrode 12 can have a roughened end surface which can provide a small electrolyte film space 36 which is maintained in the spaced relationship between the sensing electrode 12 and the membrane 16. The electrolyte film space 36 can provide minute electrolyte flow passages for maintaining electrical continuity between the sensing electrode 12 and the electrode 14.

The tension of the membrane 16 is maintained by holding down the membrane via the sleeve 22. By using an elastomer for the sleeve 22, the membrane can be fully stretched to provide a consistent layer of the electrolyte composition 24 between the sensing electrode 12 and the membrane 16. The body portion of the sleeve 22a, and lip of the sleeve 22b can provide a force both on the sides and front of the membrane 16 to retain the membrane 16 in a fixed position and retaining the spaced apart relationship between the sensing electrode 12 and the membrane 16.

The elastic nature of the sleeve 22, can also provide a steady gripping force so that the membrane can be held in a spaced apart relationship with the sensing electrode 12 securely. To further enhance the membrane tension support, a gasket 32 can be used.

The sleeve 22, made from a material such as silicone rubber tubing, retains the membrane 16 in a spaced apart relationship from the sensing electrode 12. The body portion 22a of the sleeve 22 holds the side section of the membrane 16b snugly against the sides of an electrode housing 30. The lip of the sleeve 22b draws the membrane more tightly against the housing 30 retaining the front section of the membrane 16a in a spaced apart relationship to the outer face of the sensing electrode. The sleeve 22 provides a large enough sealing contact between the membrane 16 and the electrode housing 30 in contrast to O-rings which are conventionally utilized and provide only a line sealing contact. A gasket 32 can also be placed between the membrane 16 and the lip of the sleeve 22b in order to provide an additional seal to hold the membrane in place.

The membrane 16 is preferably formed of perfluoroalkoxy-polytetrafluoroethylene (PFA-Teflon), or other highly gas permeable membranes, as for example polytetrafluoroethylene (Teflon), perfluoroalkoxy polymer, fluorinated ethylene propylene (FEP), polyethylene, polypropylene and silicone rubber.

When the polarographic sensor 10 is used for the measurement of oxygen, the sensing electrode 12 can be formed of gold, rhodium, or any noble metal. Preferably, the sensing electrode 12 is rhodium. The second electrode 14 can be formed of silver and the electrolyte 24 is then suitably a lithium chloride solution.

Referring specifically to FIG. 1, a hollow cylindrical cap 26 is formed with a central opening 28 and is threaded to the first end of the housing 30 through which extends the membrane 16 mounted on the housing 30 by the sleeve 22.

A small rubber O-ring 38, disposed in an annular recess in the cap, engages the membrane 16 when the cap is threaded on to the first end of the housing 30 and serves to tightly pull the sleeve down on to the housing 30. The small O-ring 38 in the cap may be eliminated depending on the dimension of the sensor.

A suitable polarizing potential is impressed across the electrodes from an external circuit (not shown) so that when a gas such as oxygen diffuses through the membrane 16 into the electrolyte film space 36 adjacent to the electrode 12, the oxygen is reduced at the electrode, thereby producing a current which can indicate the partial pressure of the oxygen in the sample medium being analyzed. The external voltage can be eliminated if the electrodes are formed of materials which produce an electrical voltage potential therebetween of proper magnitude. For example, the sensing electrode 12 may be formed of platinum, gold, silver, rhodium or any noble metal and the electrode 14 of zinc, cadmium, lead or silver and the electrolyte may be lithium chloride solution.

I. THE POLAROGRAPHIC SENSOR DEVICE

According to the present invention, there is provided a polarographic sensor device 10 for determining the partial pressure of a gas in a sample medium. The device comprises, a) a substantially hydroscopic electrolyte composition 24, 36 joining a pair of spaced apart electrodes 12 and 24; b) a membrane 16 permeable to gas but impermeable to the electrolyte, the membrane having a front section for separating the electrodes and the electrolyte from the sample medium; and c) a fastener comprising a sleeve 22 having a body portion 22a, and a lip 22b for retaining the membrane 16. The fastener can further comprise a gasket 32.

A. The Electrodes

The polarographic sensor device 10 comprises a pair of electrodes adapted to be joined by a substantially hydroscopic electrolyte composition. One of the pair of the electrodes is a sensing electrode. Typically the sensing electrode is a cathode. The other electrode is typically an anode.

1. The Sensing Electrode

Typically the sensing electrode is in the form of a wire which is embedded in a plastic or glass body. Preferably, the wire is embedded in a glass body. The sensing electrode typically is a cathode. The cathode can be a metal wire of platinum, gold, silver, rhodium or any noble metal. Preferably, the wire is rhodium.

When the wire is embedded in the glass body, a sufficient seal should be made. This seal can be maximized by having the wire and the glass body with similar thermal expansion coefficients. According to the present invention, the rhodium wire and the glass body have similar thermal expansion coefficient properties such that a tighter seal can be made resulting in a more accurate sensing electrode.

To prevent the electrolyte composition solution from drying out and to ensure optimal capillary effect, the cathode can be polished and contoured. Typically, the cathode can be polished to a 240–600 grit finish. Less than a 240 grit finish can result in a cathode with a rough surface and a larger current output from the electrode. Greater than a 600 grit finish can result in a small current output from the electrode. Preferably, the cathode is polished to a 320 grit finish.

2. The Second Electrode

Typically, the second electrode is a reference electrode which can also act as the anode, the part in current passing through the electrode. The second electrode can be an anode made of a wire. Typically, the wire can be made of zinc, cadmium, lead and silver. Preferably, the wire is silver.

When silver is used as the anode, and the electrolyte solution contains chloride ions, a stable silver/silver chloride (Ag/AgCl) reference electrode can be established. However, some of the silver ions generated during the usage of the sensor can be deposited on the cathode surface which can result in an unstable electrode response. This problem can be minimized in the following ways. 1) An electrolyte solution can be formulated so that the silver solubility is minimal. 2) The silver anode surface area should be large enough such that the current density at the anode is greatly decreased. 3) The silver anode surface can be coated with a thin layer of Nafion® film (Dupont Chemicals, Wilmington, Del.). Nafion® is a cationic ionomer which can trap a percentage of the silver ions generated during electrolysis so that these silver ions are not available to deposit on the cathode which can result in slow electrode response.

B. The Electrolyte Composition

The electrolyte composition is typically a substantially hydroscopic electrolyte solution. The composition of the electrolyte solution can be important in determining the stability of response of the polarographic sensor and the life time of the polarographic sensor. Electrolyte depletion can often lead to a sensor requiring frequent maintenance.

Certain characteristics of electrolyte compositions typically can include the ability of the electrolyte composition to minimize the amount of silver ions dissolving and migrating in solution. Also, the electrolyte solution should also reduce the loss of solvent, for example water, from evaporation. Oxygen reduction reactions can consume water which can lead to water loss at the electrode surface which can result in an unstable sensor. Typically, the electrolyte a) establishes a stable reference potential if silver wire is used as the anode b) provides a reasonable wide potential range within which the oxygen reduction current is stable and independent of the bias potential applied c) reduces the loss of solvent, i.e., water d) eliminates crystallization in the vicinity of the cathode surface e) prevents silver ions generated at the electrode surface from dissolving and migrating into the electrolyte solution f) has an oxygen reduction current which is linear with oxygen tension and g) is sufficient such that the residual current of the oxygen polarographic sensor is low.

Typically, the buffering capacity and pH of the electrolyte solution are not significant factors since the pH in the vicinity of the cathode soon becomes alkaline due to hydroxide ion formation once the sensor is in use.

The depletion of solvent from the electrodes can lead to increases in the ohmic resistance of the electrodes, resulting in a decreased oxygen reduction current.

Typically, a substantially hydroscopic composition such as potassium chloride (KCl) or lithium chloride (LiCl) can be used as the electrolyte composition. Preferably, lithium chloride is used. Lithium chloride can be substantially more hydroscopic than potassium chloride, thus the loss of water can be slower when lithium chloride is used.

Typically, the concentration range of lithium chloride is from about 0.02M to about 0.2M. Preferably, the concentration range is 0.02M to about 0.10M. More preferably, 0.025M lithium chloride is used as the electrolyte composition. Greater than 0.2M lithium chloride can result in Ag poisoning of the sensing electrode. Less than 0.02M can result in an insufficient reference voltage which can change the stability of the electrode.

The existence of chloride ions in the electrolyte solution can establish a stable silver/silver chloride (Ag/AgCl) reference electrode potential. The relatively low concentration of lithium chloride can decrease the amount of AgCl formed at the anode to be dissolved into the solution by forming a $AgCl_2$ complex, which can eliminate the formation of LiCl crystals at the cathode area and which can result in a sensor with slow response.

The electrode output typically is in the nano-Amp range for the present application. Therefore the "ohmic drop" which can be caused by a relatively high solution resistance should not be a factor.

Typically, during the anode reaction, the chloride ion concentration decreases as it is being used by the anode. Hydroxide ions are produced as a result of oxygen reduction and silver oxide can be generated at the anode surface. Thus, the reaction at the anode can be faster if the initial chloride concentration is low.

However, since the reference voltages for Ag/AgCl (+0.22V) and $Ag/Ag_2O$ (+0.35V) only differ by 130 mV, the bias potential applied at the cathode is carefully chosen so that the oxygen reduction is independent of bias voltage. The electrode output is basically unaltered by this change in reference potential.

The membrane of the polarographic sensor is relatively impermeable to the electrolyte, yet the membrane can be somewhat permeable to water vapor. Thus, when the sensors are exposed to air or other gaseous mediums over an extended period of time, water vapor from the electrolyte composition can diffuse out of the sensor through the membrane. Therefore, the electrolyte solution can further include additional additives to maintain the polarographic sensors performance and stability by helping to retain the moisture of the electrolyte solution so that the sensor does not dry out. Typically, a thin layer of an air pocket can be formed between the sensing electrode and the membrane when filling the electrolyte composition solution into the electrode housing. This can result in a substantially low (close to zero) current output. A suitable wetting agent such as Triton X-100 or Surfynol 104 can be used to eliminate the air pocket formations.

Additionally, the electrolyte composition solution can include glycerol or ethylene glycol. Typically, solutions containing glycerol can have higher boiling points and can decrease solvent evaporation. Additionally, glycerol can also be used as a wetting agent and can be used to prevent the cathode surface from drying out which can lead to polarographic sensor deterioration. Typically, the concentration range for glycerol is from about 5% to about 20%. Preferably, 10% glycerol is used. Greater than 20% glycerol present can result in slow electrode response. Less than 10% glycerol can be ineffective to retain moisture of the electrolyte.

Ethylene glycol can be used in place of glycerol in the electrolyte composition. The concentration range of ethylene glycol is preferably 33% because at this concentration level, ethylene glycol can be efficient in preventing the electrolyte from drying out at the interface between the gas permeable membrane and the sensing electrode surface.

C. The Membrane

Typically, the membrane is permeable to gas but impermeable to the electrolyte. It is desirable to select the gas permeable membrane as a diffusion barrier which is as thin as possible and made of a material having a good diffusion constant in order that the shortest possible response time for the sensing electrode can be achieved when there is a change in the gas concentration of the sample medium. The membrane can be polytetrafluoroethylene (i.e. Teflon), polyethylene, polypropylene, silicon rubber, mylar, fluorinated ethylene propylene (FEP), and perfluoroalkoxy polymer, including perfluoroalkoxy-polytetrafluoroethylene (PFA-Teflon). Preferably, the membrane is PFA-Teflon. PFA-Teflon has characteristics that can allow relatively rapid passage of some components that are commonly analyzed, such as oxygen, and carbon dioxide, yet is relatively impermeable to electrolytes.

The thickness of the membrane typically is from 1 mil to about 3 mils. Preferably, the thickness of the membrane is about 1 mil.

Preferably, the membrane is stretched and stressed to the point where the membrane just begins to show the whitening characteristics of crystallization in order to improve signal to noise ratios. The membrane should be maintained throughout the storage shelf-life of the polarographic sensor. Furthermore, membrane deterioration can also lead to a sensor requiring frequent maintenance.

Preferably, the polarographic sensor contains only a single membrane. Typically, with two membranes, a gap can exist between a hydrophilic inner membrane close to the cathode and the outer membrane which can result in slow electrode response. By utilizing one membrane, this problem can be eliminated.

D. The Fastener

The fastener can comprise a sleeve with a body portion and a lip for retaining the membrane and mounting the membrane on the electrode housing. The tension of the membrane is maintained by holding the membrane down via the sleeve. The membrane separates the electrodes and the electrolyte from the sample medium. The sleeve maintains a spaced apart relationship between the membrane and the sensing electrode.

Typically the sleeve is made of an elastomer to provide a steady gripping force so that the membrane can be secured in a spaced apart relationship with the sensing electrode. The membrane can be fully stretched to provide a consistent film layer of the electrolyte composition 24 between the sensing electrode 12 and the membrane 16.

To further enhance the membrane tension support, a gasket 32 can be used to retain the membrane. The gasket should not be too compressible such that variations occur in the tension of the membrane that can change the spaced apart relationship between the membrane and sensing electrode. Furthermore, during reactions, the sample medium typically is stirred. Over time, the membrane can become loose and can flap, resulting in increased background noise. The gasket can substantially alleviate this potential problem by providing additional support for the membrane thereby eliminating the need for an additional membrane as support. Typically, the gasket can be made from any perfluoalkoxy polymer (PFA). Preferably, the gasket is made from 10 mil PFA to provide support for the membrane.

The spaced apart relationship between the membrane and the sensing electrode has characteristics that makes it particularly advantageous for determining the long service life of the polarographic sensor.

The thickness of the electrolyte film layer typically is controlled by the distention of the sensing electrode toward the membrane. The roughness of the surface end of the sensing electrode can determine the spaced apart relationship. A rougher surface can provide a larger spaced relationship, and a polished surface can provide a thinner electrolyte film layer. If the membrane tension changes, the spaced apart relationship and the electrolyte layer between the sensing electrode and the membrane can also change, thus creating a change in the electrode response.

The preferred distention of the sensing electrode is 10±5 mils to provide an electrolyte layer enough to contribute to a fast electrode response. A thick electrolyte film layer can result in a large gap between the sensing electrode and the membrane which can result in slower electrode response. In addition, the membrane typically should be substantially taut which could bypass the need to change the electrode frequently.

In addition, an adequate seal of the electrolyte composition reservoir 24 with respect to the electrode housing must be provided for the assembled condition. The membrane typically should not be expanded too greatly during mounting the membrane such that the membrane's diffusion characteristics for the gas component to be determined is not changed in an unwanted manner or that capillary-like expansion fissures are formed from which the electrolyte can escape unnoticed during storage or operation.

Furthermore, the spaced apart relationship between the membrane 16 and the sensing electrode 12 should remain relatively constant even when there are pressure fluctuations of appreciable magnitude in the sample medium. This spaced apart relationship can alleviate a problem known to those skilled in the art as the "stirring effect". The constant stirring of the sample medium can produce pressure fluctuations of significant magnitude which can interfere with the sensing electrode which can result in high background noise and inaccurate readings.

II. USE OF THE POLAROGRAPHIC SENSOR DEVICE

Typically, the polarographic sensor device just described, can be immersed into a sample medium of a partial pressure of the gas to be determined. A suitable voltage can be applied across the electrodes. The current passed between the electrodes can be proportional to the partial pressure of the gas in the sample.

The polarographic sensor device 10, typically relies on the measurement of true instantaneous rate at very early stages of a reaction in a sample medium. Typically the maximum rate is obtained in a relatively short time interval of the order of 10 seconds to 10 minutes. Direct rate sensing with the polarographic sensor device 10 is further applicable to concentration and activity determinations and to very low levels of concentration determinations.

With reference to the enzymatic assay for glucose in blood and urine, the polarographic sensor device 10 can directly monitor oxygen consumed in a glucose oxidase-glucose reaction and does not require preliminary purification or deproteinization of the sample. In the analysis of blood or urine glucose, equal volume portions of blood or urine samples are added to a single batch of buffered glucose oxidase solution. The solution is stirred and the reaction proceeds in the presence of the device 10 providing an electrical response linear with respect to oxygen concentration. The electrical response can be converted into a signal proportional to the time rate of change of oxygen and this signal is recorded. The maximum recorded signal determines the quantity of glucose initially present.

In order that the present invention may be more fully understood, the following Examples and comparative results are given by way of illustration only.

EXAMPLES

Example I

The usable life of a polarographic sensor can be measured by the stability of the electrode output current. Beckman's Synchron CX® 3 and CX® 3 Delta analyzers were used in the experiments. The electrode current used software gain settings within the operation software defined range for the instrumentation (18–45 nano Amps).

The polarographic oxygen sensors used were the ones described in this invention. The polarographic oxygen sensors had Teflon membranes and electrolyte solutions made from 0.025M LiCl. Typically, the electrolyte composition contained 0.1M sodium bicarbonate, 0.01M sodium carbonate, 0.025M lithium chloride and 10% glycerol.

Glucose determination on the Synchron CX® 3 and CX® 3 Delta used the oxygen rate method developed by Beckman Instruments, Inc. (Brea, Calif.). A conventional Beckman rechargeable oxygen electrode and four Beckman polarographic oxygen sensors were used to measure the rate of change in oxygen consumption when a sample was injected into an enzyme reagent solution.

A 10 microliter sample was injected into an enzyme reagent solution causing the glucose to undergo change according to the following reaction:

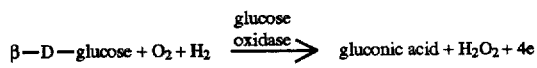

In the reaction, oxygen was consumed at the same rate as the glucose reacted to form gluconic acid. At all times during the reaction, the rate of oxygen consumption was directly proportional to the concentration of glucose present in the reaction cup. The observed rate, attained after a brief interval required for reagent mixing and system response, has been shown to be a direct measure of the concentration of glucose originally present in the sample at the time of the sample injection. Because, oxygen consumption rather than peroxide formation is measured, the only requirement for peroxide is that it must be destroyed by a path not leading back to oxygen. The addition of ethanol to the reagent causes peroxide to be destroyed catalase without yielding oxygen, according to the following reaction:

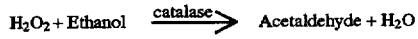

Figure 3:
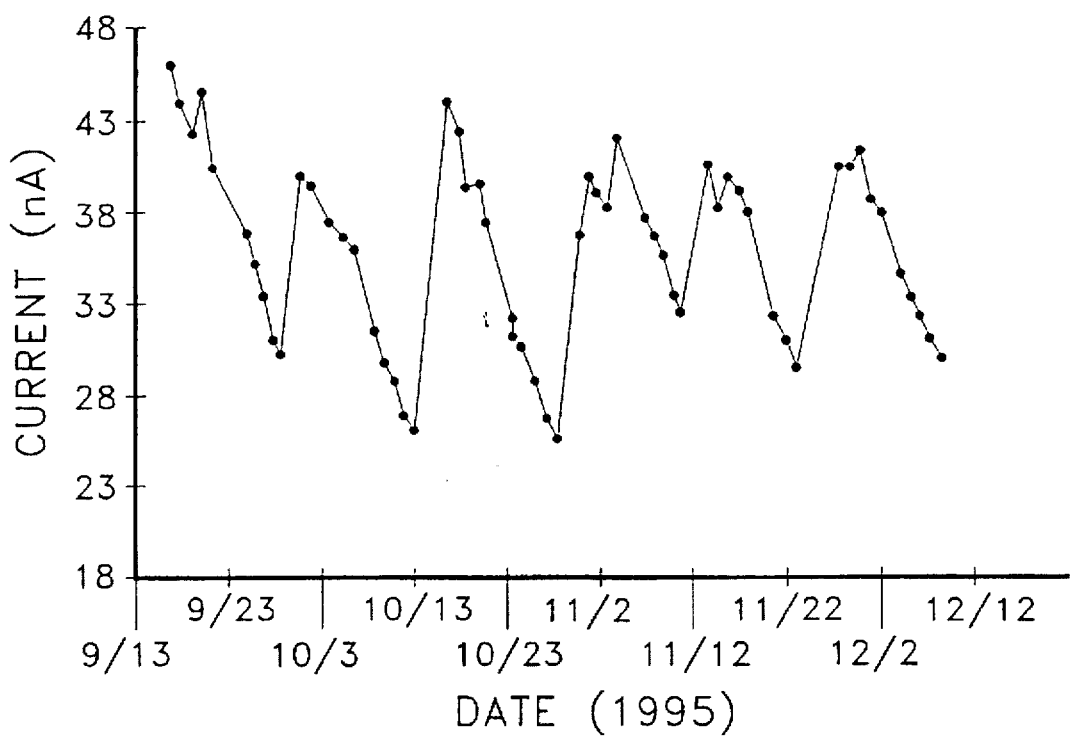
FIG. 3 is a graph showing the electrode stability of a Beckman rechargeable oxygen electrode as a glucose sensor used on a Synchron CX® 3 analyzer (Beckman Instruments, Inc., Brea, Calif.)
Figure 4:
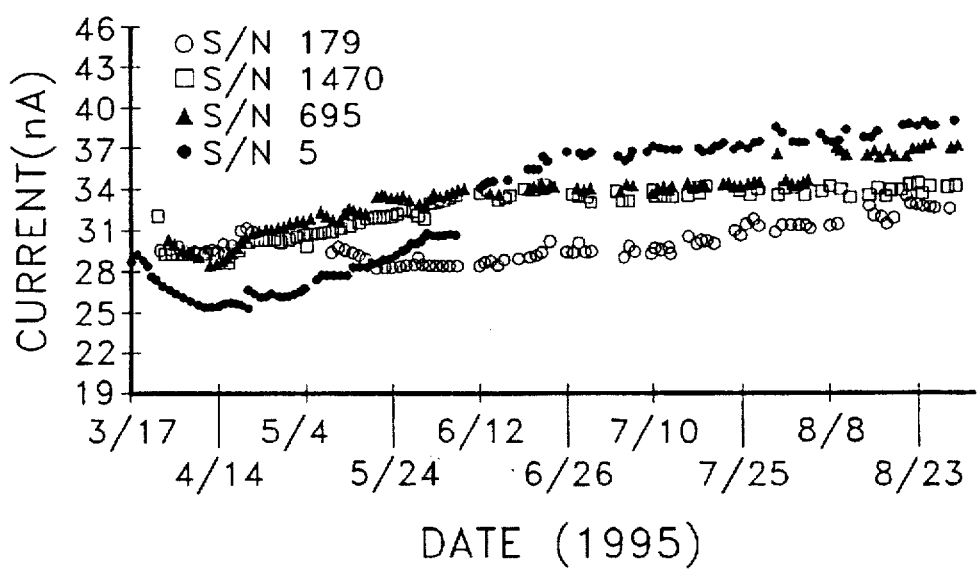
FIG. 4 is a graph showing the electrode stability of a Beckman polarographic oxygen sensors as glucose sensors used on Synchron CX® 3 and CX® 3 Delta analyzers (Beckman Instruments, Inc., Brea, Calif.)

Referring now to FIG. 3 is a graph showing the electrode stability of a Beckman rechargeable oxygen electrode used on a Synchron CX® 3 analyzer as a glucose sensor. The current (measured in nano Amps (nA)) was measured over a 3 month period. Every two weeks, the electrode membrane and electrolyte solution had to be changed due to the drastic decrease in current. Now referring to FIG. 4 is a graph showing the electrode stability of Beckman polarographic oxygen sensors used on Synchron CX® 3 and CX® 3 Delta analyzers as glucose sensors. This graph also shows the current (nA) being measured, however, these polarographic oxygen sensors were stable for a 5 month period of time compared to the Beckman rechargeable oxygen electrode (FIG. 3). Two of the polarographic oxygen sensors were measured on the Synchron CX® 3 analyzers (S/N 179 and S/N 1470) and two of the polarographic oxygen sensors were measured on the CX® 3 Delta analyzers (S/N 695 and S/N 5). The results show that over a 5 month period of time, the polarographic oxygen sensors remained quite stable (current averaging between 25 nA and 39 nA) as compared to the spurious current readings as compared to the Beckman rechargeable oxygen electrode (FIG. 3). Furthermore, for the polarographic oxygen sensors, the membrane and the electrolyte solution did not have to be changed during the 5 months as compared to the Beckman oxygen electrode. These polarographic sensors were used after 5 months on Synchron CX® 3 and CX® 3 Delta analyzers without recharging or maintenance.

Example II

Synchron analyzers available from Beckman Instruments, Inc. utilize an oxygen depletion rate method for blood glucose measurement. Preferably the electrode should have a fast response, have a stable oxygen baseline and preferably the polarographic sensor is insensitive to the stirring effect. Preferably, these criteria must be maintained throughout the polarographic service life. The results shown in FIG. 5 show the glucose recoveries of Beckman's Synchron controls on Synchron CX® 3 and CX® 3 Delta instruments.

Three Beckman Synchron analyzer glucose control solutions; 45 mg/dl, 210–220 mg/dl and 360–390 mg/dl. One polarographic oxygen sensor (CX® 3 S/N 1470) was used on a Synchron CX® 3 analyzer and one polarographic oxygen sensor (CX® 3 Delta S/N 95) was used on a Synchron CX® 3 Delta analyzer (see FIG. 5). FIG. 5 is a graph showing glucose control recovery using Beckman polarographic oxygen sensors used on a Synchron CX® 3 and CX® 3 Delta analyzers as glucose sensors.

Figure 5:
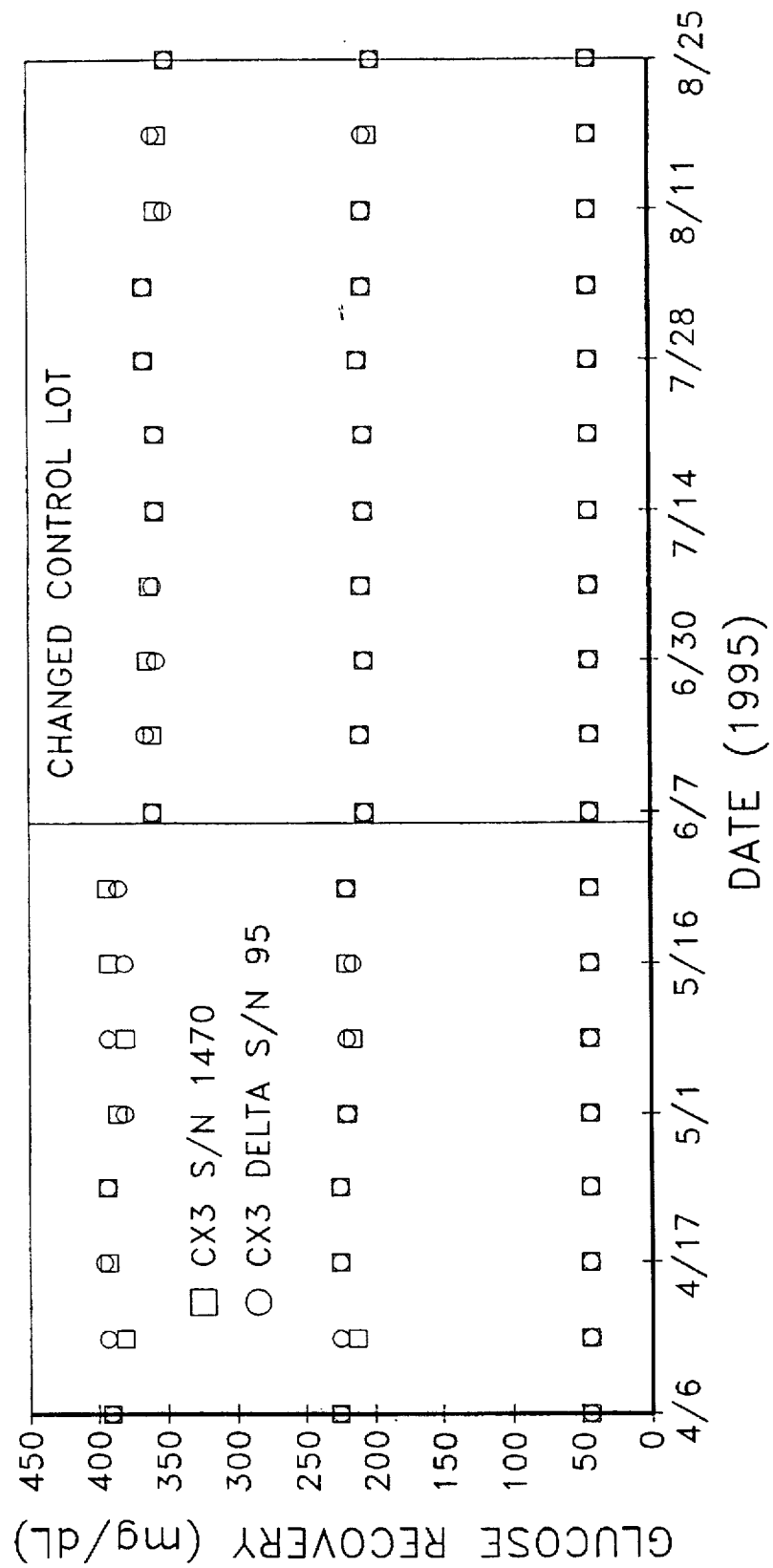
FIG. 5 is a graph showing glucose control recovery using Beckman polarographic oxygen sensors as glucose sensors used on Synchron CX® 3 and CX® 3 Delta analyzers.

The results in FIG. 5 show that these polarographic sensors produced consistent glucose recovery and also generated satisfactory linearity and precision data over a 5 months testing period.

The present invention provides a polarographic sensor device of improved sensitivity and selectivity. In particular, this device offers a number of advantages in comparison to conventional polarographic sensors. These polarographic sensors are accurate in detecting and measuring the partial pressure of a gas in a sample medium. Preferably, these polarographic sensors are particularly suited for measurement of blood glucose in an oxygen depleted reaction, but can be used for measurement of other gases in other enzymetic assays. In addition, the sleeve for capturing and securing the membrane in a spaced apart relationship, bypasses the problems associated with inadequate membrane seals. These types of polarographic sensors have low maintenance and exhibit high performance for prolonged periods of time (greater than three months).

Although the present invention has been described in considerable detail with reference to certain preferred versions, other versions are possible. Thus, the spirit and the scope of the appended claims should not be limited to the description of the preferred versions contained herein.

What is claimed is:

1. A polarographic sensor device for determining the partial pressure of a gas in a sample medium, the device comprising:

a) a substantially hydroscopic electrolyte composition having an electrolyte concentration of less than about 0.2M joining a pair of spaced apart electrodes, one of the pair of electrodes being a sensing electrode;

b) a membrane permeable to gas but impermeable to the electrolyte, the membrane having a front section for separating the electrodes and the electrolyte from the sample medium; and c) a fastener comprising a sleeve that retains the membrane in a fixed position and in a spaced apart relationship from the sensing electrode, and that maintains a tension of the membrane, wherein the sleeve comprises a body portion and a lip, the body portion retaining a side section of the membrane in a fixed position against a side of a housing, and the lip retaining a portion of the front section of the membrane in a fixed position, maintaining tension over the front section of the membrane; and holding substantially the entire front section of the membrane in a spaced apart relationship from the sensing electrode.

2. The device as defined in claim 1, wherein the membrane is selected from the group consisting of polyethylene, polypropylene, a polymer of a fluorinated alkane, fluorinated ethylene propylene (FEP), silicone rubber, polytetrafluoroethylene, and perfluoroalkoxy polymer.

3. The device as defined in claim 2, wherein the perfluoroalkoxy polymer comprises perfluoroalkoxy-polytetrafluoroethylene.

4. The device as defined in claim 1, wherein the membrane has gas permeability characteristics approximating the gas permeability characteristics of perfluoroalkoxy-polytetrafluoroethylene.

5. The device as defined in claim 1, wherein the thickness of the membrane is from about 1 mil to about 3 mils.

6. The device as defined in claim 5, wherein the thickness of the membrane is about 1 mil.

7. The device as defined in claim 1, wherein the gas is selected from the group consisting of oxygen and carbon dioxide.

8. The device as defined in claim 1, wherein the sensing electrode is a cathode.

9. The device as defined in claim 8, wherein the cathode is a wire.

10. The device as defined in claim 9, wherein the wire is selected from the group consisting of platinum, gold, silver and rhodium.

11. The device as defined in claim 10, wherein the wire is rhodium.

12. The device as defined in claim 1, wherein the second electrode is an anode.

13. The device as defined in claim 12, wherein the anode is a wire.

14. The device as defined in claim 13, wherein the wire is selected from the group consisting of zinc, cadmium, lead and silver.

15. The device defined in claim 14, wherein the wire is silver.

16. The device of claim 1, wherein the electrolyte composition is selected from the group consisting of potassium chloride and lithium chloride.

17. The device as defined in claim 16, wherein the electrolyte composition comprises lithium chloride.

18. The device as defined in claim 17, wherein the lithium chloride has a concentration from about 0.02M to about 0.2M.

19. The device as defined in claim 18, wherein the lithium chloride has a concentration from about 0.02M to about 0.10M.

20. The device as defined in claim 19, wherein the lithium chloride has a concentration of 0.025M.

21. The device as defined in claim 1, wherein the sleeve is elastomeric.

22. The device as defined in claim 1, wherein the fastener further comprises a gasket positioned between the membrane and the lip of the sleeve, and wherein the gasket provides added tension support to the membrane and further retains the membrane in place and in a spaced apart relationship from the sensing electrode.

23. The device as defined in claim 1, wherein the electrolyte composition further includes glycerol or ethylene glycol.

24. The device as defined in claim 23, wherein the glycerol has a concentration from about 5% to about 20%.

25. The device as defined in claim 24, wherein the glycerol concentration is about 10%.

26. A method for determining the partial pressure of a gas in a sample medium comprising:

a) contacting the sample medium with the device of claim 1;

b) applying a voltage across the electrodes;

c) measuring a current generated between the electrodes, the current being proportional to the partial pressure of the gas in the sample; and d) determining the partial pressure of the gas in the sample medium.

27. The device as defined in claim 1, wherein the polarographic sensor device further comprises a cap having a central opening, the cap being coupled to an end of the housing through which the membrane extends, and wherein the cap further retains the membrane and further maintains the tension of the membrane.

28. The device as defined in claim 1, wherein the polarographic sensor device has a continuous service life for a period of time greater than three months.

29. The device as defined in claim 28, wherein the polarographic sensor device has a continuous service life for a period of time greater than five months.

30. A polarographic sensor device for determining the partial pressure of a gas in a sample medium, the device comprising:

a) a substantially hydroscopic electrolyte composition having an electrolyte concentration of less than about 0.2M joining a pair of spaced apart electrodes, the electrolyte composition being from about 0.02M to about 0.1M lithium chloride, wherein one of the pair of electrodes is a sensing electrode;

b) a membrane permeable to gas but impermeable to the electrolyte, the membrane having a front section for separating the electrodes/and the electrolyte from the sample medium; and, c) a fastener comprising an elastomeric sleeve that retains the membrane in a fixed position and in a spaced apart relationship from the sensing electrode, and that maintains a tension of the membrane, wherein the sleeve comprises a body portion and a lip, the body portion retaining a side section of the membrane in a fixed position against a side of a housing, and the lip retaining a portion of the front section of the membrane in a fixed position, maintaining tension over the front section of the membrane, and holding substantially the entire front section of the membrane in a spaced apart relationship from the sensing electrode.

31. The device as defined in claim 30, wherein the fastener further comprises a gasket positioned between the membrane and the lip of the sleeve, and wherein the gasket provides added tension support to the membrane and further retains the membrane in place and in a spaced apart relationship from the sensing electrode.

32. The device as defined in claim 30, wherein the polarographic sensor device further comprises a cap having a central opening, the cap being coupled to an end of the housing through which the membrane extends, and wherein the cap further retains the membrane and further maintains the tension of the membrane.

33. A polarographic sensor device for determining the partial pressure of a gas in a sample medium, the device comprising:

a) a housing having an internal cavity, a first end, and an outer surface;

b) a substantially hydroscopic electrolyte composition having an electrolyte concentration of less than about 0.2M joining a pair of spaced apart electrodes disposed inside the housing, one of the pair of electrodes being a sensing electrode;

c) a membrane permeable to gas but impermeable to the electrolyte, the membrane having a front section enclosing the first end of the housing; and d) a fastener comprising an elastomeric sleeve that retains the membrane in a fixed position and in a spaced apart relationship from the sensing electrode, and that maintains a tension of the membrane, wherein the sleeve comprises a body portion and a lip, the body portion retaining a side section of the membrane in a fixed position to the outer surface of the housing, and the lip retaining a portion of the front section of the membrane in a fixed position, maintaining tension over the front section of the membrane, and holding substantially the entire front section of the membrane in a spaced apart relationship from the sensing electrode; and, wherein the fastener further comprises a gasket positioned between the membrane and the lip of the sleeve, and wherein the gasket provides added tension support to the membrane and further retains the membrane in place and in a spaced apart relationship from the sensing electrode.

34. The device as defined in claim 33, wherein the polarographic sensor device further comprises a cap having a central opening, the cap being coupled to the first end of the housing through which the membrane extends, and wherein the cap further retains the membrane and further maintains the tension of the membrane.

* * * * *